United States Patent

Shehata et al.

[11] Patent Number: 5,997,564
[45] Date of Patent: Dec. 7, 1999

[54] FEMORAL COMPRESSION DEVICE FOR POST-CATHETERIZATION

[75] Inventors: Nader Shehata; Emiliano Cafueri; Silvio Klugmann, all of Triesta, Italy

[73] Assignee: I.B.S. International Biomedical Systems, S.r.l., Trieste, Italy

[21] Appl. No.: 08/875,893

[22] PCT Filed: Nov. 17, 1995

[86] PCT No.: PCT/IT95/00194

§ 371 Date: Nov. 20, 1997

§ 102(e) Date: Nov. 20, 1997

[87] PCT Pub. No.: WO97/18763

PCT Pub. Date: May 29, 1997

[51] Int. Cl.[6] .................................................. A61B 17/08
[52] U.S. Cl. ..................................... 606/201; 606/203
[58] Field of Search .................................. 606/201–204, 606/204.15, 204.25, 204.35, 204.45, 204.55; 600/485, 490.492

[56] References Cited

U.S. PATENT DOCUMENTS 5,133,734  7/1992  Lee .
5,304,186  4/1994  Semler et al. ............................ 606/201
5,304,201  4/1994  Rice ........................................ 606/201

FOREIGN PATENT DOCUMENTS 0 082 009   6/1983   European Pat. Off. .
0 462 088  12/1991   European Pat. Off. .
2 664 807   1/1992   France .

*Primary Examiner*—Glenn K. Dawson
*Attorney, Agent, or Firm*—Browdy and Neimark

[57] ABSTRACT

A femoral arterial or venous compression device for post-catheterization hemostasis includes a supporting frame (base (1), shaft (2) and arm (4)), and an inflatable unit (carriage (6), bellows (7), disk (8), and pad (9)). The supporting frame is fixed on the human body in line with the incision site in order to bring the pad (9) exactly over and in touch with the latter. The bellows (7) are inflated thus compressing the incision site with the pad (9) for all the time needed to reach complete hemostasis. The pressure on the incision remains constant during the compression period and can be regulated and monitored using a medical sphygmomanometer.

2 Claims, 2 Drawing Sheets

FEMORAL COMPRESSION DEVICE FOR POST-CATHETERIZATION

BACKGROUND OF THE INVENTION

1. Technical Field

The invention relates to a femoral arterial or venous compression device for post-catheterization hemostasis comprised of a supporting frame, for fixing on the human body, carrying an inflatable unit which ends with a pad.

Femoral compression (compression of an incision site on the femoral artery or vein) is a step usually performed following angioplasty where enlarging the lumen of stenotic arteries takes place, thereby improving distal flow. In PTCA (Percutaneous Transluminal Coronary Angioplasty), inserting catheters via the percutaneous femoral approach is widely used to reach stenoses. Clearly, when the catheters are withdrawn from the femoral artery after the end of angioplasty procedure, the incision site must be tamponed for hemostasis. Due to the wide diameter of the femoral artery and to the anti-coagulant solution usually used in the blood during such procedures, hemostasis can only be reached applying constant pressure on the incision site for relatively long time.

2. Prior Art

The most practiced way is the manual one where an operator applies this pressure using a normal tampon. Obviously, it is a waste of time for personnel to complete hemostasis in the time required. Furthermore, the pressure practiced manually is never constant.

OBJECT AND SUMMARY

The invention as claimed is intended to remedy these drawbacks. It offers a simple method for applying constant pressure on the incision site of the femoral artery or vein occupying few minutes of personnel time.

The advantages offered by the invention are mainly that once the device is fixed on the human body, it maintains its position for all the time needed to reach hemostasis applying a constant pressure on the incision site thus stanching completely any blood flow or fluid leakage. Furthermore, the pressure applied can be regulated and monitored using a normal sphygmomanometer. Another important advantage of the device is that, during its application on the human body, the operator has a clear view of the incision site which permits an exact and effective positioning.

BRIEF DESCRIPTION OF DRAWINGS

The main parts of the device are described below with reference to the following drawings.

DETAILED EMBODIMENTS OF THE PREFERRED EMBODIMENT(S) OF THE INVENTION

Figure 1:
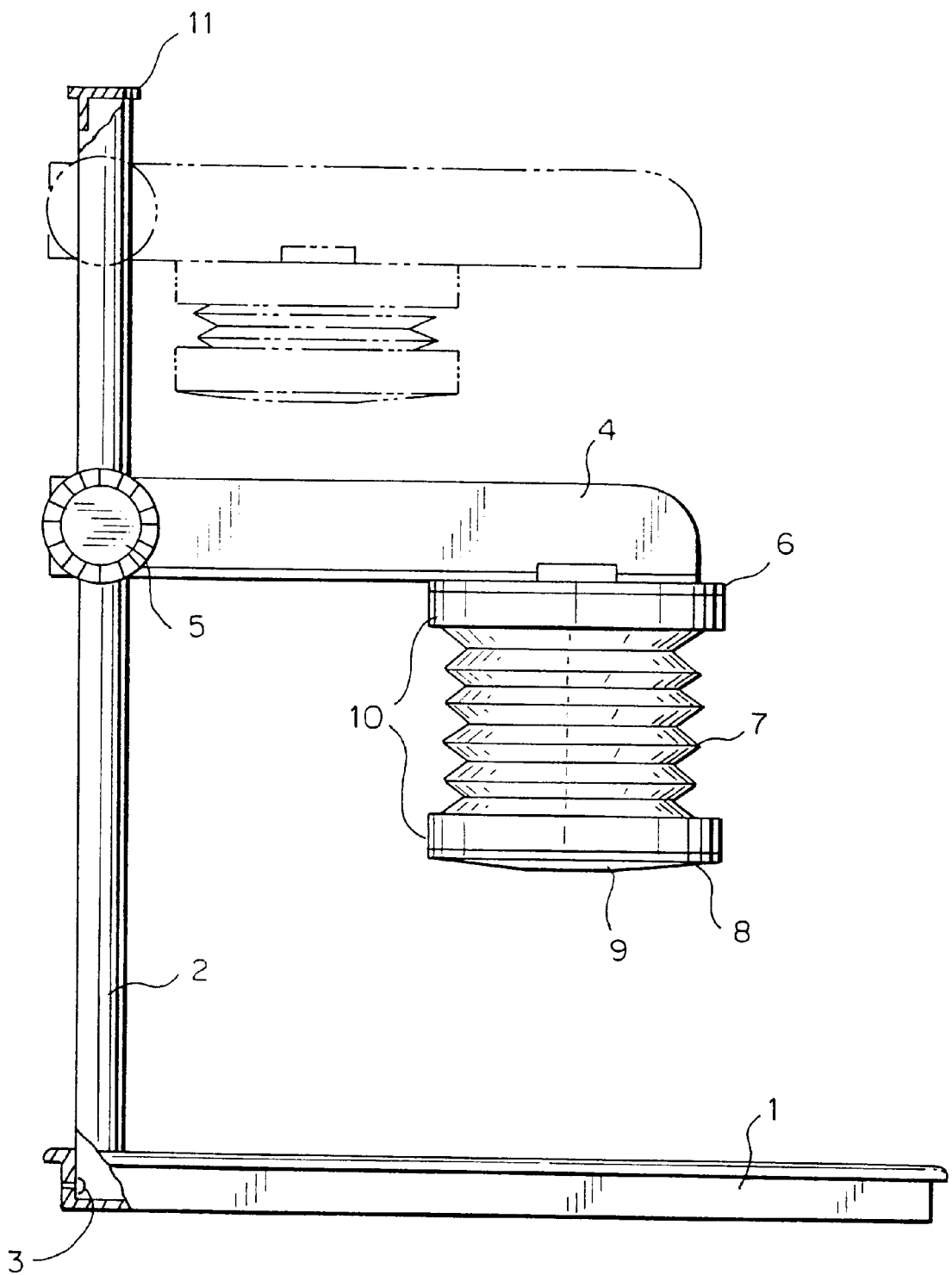
FIG. 1 is a side view on a reduced scale of the device when assembled.
Figure 2:
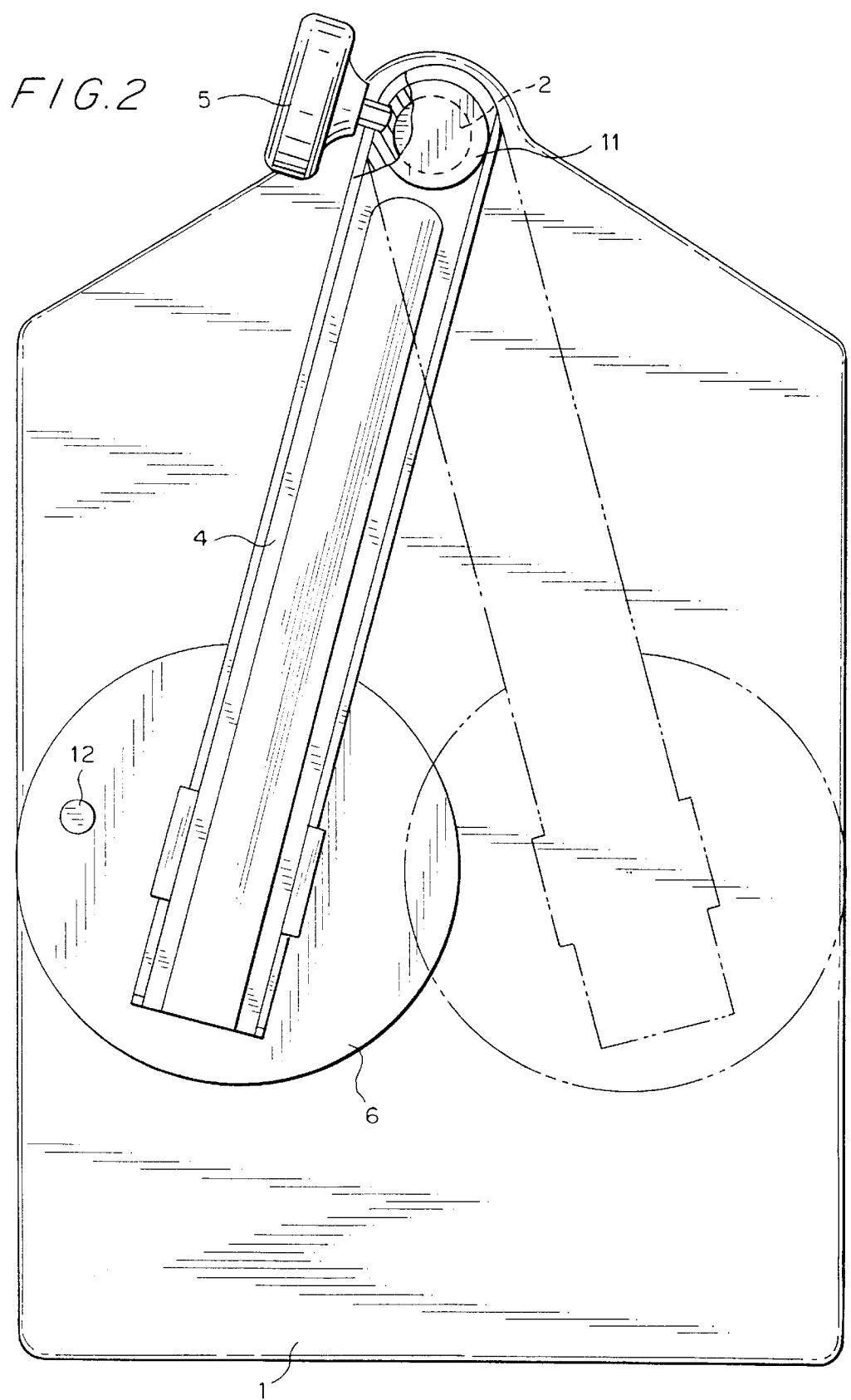
FIG. 2 is a plan on a real scale.

FIG. 1 shows the femoral compression device comprising a horizontal base (1) on which a tubular shaft (2) is fixed vertically via fastening means (3) (e.g. pin or screw). The top of the shaft is covered using a plug (11). An arm (4) can slide vertically along the shaft (2), furthermore, it can rotate in a horizontal plane, as shown in FIG. 2. The arm (4) is locked in its position using a knob (5).

Along this arm (4), a circular carriage (6) can slide horizontally, as shown in FIG. 1, carrying cylindrical bellows (7). The carriage (6) is provided on its top with a standard connection (12), as shown in FIG. 2, for connecting a medical sphygmomanometer. On the bottom side of the bellows (7) a circular disk (8) is fixed carrying, on its lower side, a pad (9) with a spherical segment shape. The carriage (6) and the disk (8) are attached to the bellows (7) using circular rings (10) as shown in FIG. 1.

The arm (4), the carriage (6), The bellows (7), the disk (8), the rings (10) and the pad (9) are made of transparent material to allow the operator to have a clear view of the incision site, this permits an exact and effective positioning of the pad (9).

BEST MODE FOR CARRYING OUT THE INVENTION

The operation of the device is as follows. The base (1) is inserted under the hip (right or left) in such a position that the vertical shaft (2) touches the external side of the hip almost in line with the incision site. Subsequently, the positions of both the arm (4) and the carriage (6) are regulated vertically and horizontally, respectively, in order to bring the pad (9) exactly over and in touch with the incision site. The position reached is maintained by locking the knob (5).

After the positioning procedure, the bellows (7) are inflated via the connection (12) using a medical sphygmomanometer thus compressing the incision site with the pad (9). Once the necessary pressure for stanching the blood flow is reached, the device can be left in its position for the time needed to reach complete hemostasis.

We claim:

1. A femoral arterial or venous compression device for post-catheterization hemostasis comprising a base (1), a vertical tubular shaft (2) fixed on said base (1) by a fastening means (3), an arm (4) slidable vertically along said shaft (2) and lockable in position by a tightening knob (5) and a circular carriage (6) slidable horizontally along said arm (4), wherein said carriage (6) holds an inflatable cylindrical bellows (7); a lower end of said bellows (7) attached to a circular disk (8) holding a spherical segment-shaped pad (9); said bellows (7) being respectively fixed at opposite ends thereof to said carriage (6) and to said disk (8) by circular rings (10); said carriage (6) being provided on a top with a connection (12) for connecting a medical sphygmomanometer to inflate said bellows (7).

2. A femoral arterial or venous compression device according to claim 1, wherein the arm (4), the carriage (6), the bellows (7), the disk (8), the pad (9) and the rings (10) are made of transparent material to allow clear viewing of the incision site.

* * * * *